US011859236B2

(12) United States Patent
Tan et al.

(10) Patent No.: US 11,859,236 B2
(45) Date of Patent: Jan. 2, 2024

(54) **METHOD FOR DETECTING L-SERINE BASED ON CYSTEINE DESULFURASE-CONTAINING LIVING *ESCHERICHIA COLI* CELL**

(71) Applicant: WENZHOU MEDICAL UNIVERSITY, Wenzhou (CN)

(72) Inventors: Guoqiang Tan, Wenzhou (CN); Jianghui Li, Wenzhou (CN); Feng Liang, Wenzhou (CN); Yilin Pang, Wenzhou (CN)

(73) Assignee: WENZHOU MEDICAL UNIVERSITY, Zhejiang (CN)

( * ) Notice: Subject to any disclaimer, the term of this patent is extended or adjusted under 35 U.S.C. 154(b) by 0 days.

(21) Appl. No.: 17/811,600

(22) Filed: Jul. 11, 2022

(65) Prior Publication Data
US 2023/0159980 A1 May 25, 2023

(30) Foreign Application Priority Data

Nov. 1, 2021 (CN) .......................... 202111282167.8

(51) Int. Cl.
*C12Q 1/48* (2006.01)
*C12N 9/10* (2006.01)
*C12N 15/70* (2006.01)

(52) U.S. Cl.
CPC ................ *C12Q 1/48* (2013.01); *C12N 9/13* (2013.01); *C12N 15/70* (2013.01); *C12Y 208/01007* (2013.01); *C12N 2800/101* (2013.01)

(58) Field of Classification Search
CPC ........ C12N 15/70; C12N 9/13; C07K 14/245; C12Q 1/48; C12Y 208/01007; G01N 33/6812; G01N 33/6815
See application file for complete search history.

(56) References Cited

U.S. PATENT DOCUMENTS

2023/0145499 A1* 5/2023 Tan ..................... G01N 33/6812
435/193

FOREIGN PATENT DOCUMENTS

CN 110967305 A * 4/2020
EP 323068 A2 * 7/1989

OTHER PUBLICATIONS

Moore, S. & Stein, W.H. Photometric Ninhydrin Method for Use in the Chromatography of Amino Acids, Journal of Biological Chemistry, 176(1) 367-388 (Year: 1948).*
Sharma, N. et al. A Quick and Easy Method for Making Competent *Escherichia coli* Cells for Transformation Using Rubidium Chloride. Bio-Protocol. [online]. vol. 7, No. 21, p. 1-6. [retrieved on Jul. 3, 2023]. DOI: 10.21769/BioProtoc.2590 (Year: 2017).*
Kim, JH, Tonelli, M, & Markley, JL. Disordered form of the scaffold protein IscU is the substrate for iron-sulfur cluster assembly on cysteine desulfurase. Proc Natl Acad Sci U S A. Jan. 10, 2012;109(2):454-9. (Year: 2012).*
Scopes, R. Enzyme Activity and Assays. Encyc. of Life Sciences. Jul. 11, 2002; 1-6. https://doi.org/10.1038/npg.els.0000712 (Year: 2002).*
Binkley, F. On the Nature of Serine Dehydrase and Cysteine Desulfurase. J Biol Chem. (1943), 150, 261-262 (Year: 1943).*
BioVision Incorporated. DL-Serine Assay Kit (Fluorometric) [online]. Jul. 6, 2017. [retrieved on Jul. 3, 2023] Retrieved from Internet <URL: https://www.biovision.com/documentation/datasheets/K743.pdf> (Year: 2017).*
Liger, Dominique. 'Re: What are the ideal conditions for inducing pBAD promoter?'. In ResearchGate [online]. Nov. 2014; [retrieved on Jul. 3, 2023]. URL: https://www.researchgate.net/post/What-are-the-ideal-conditions-for-inducing-pBAD-promoter/5463515fd5a3f28d038b466c/citation/download (Year: 2014).*
Lu J, et al. Complementary roles of SufA and IscA in the biogenesis of iron-sulfur clusters in *Escherichia coli*. Biochem J. Jan. 15, 2008;409(2). 535-543. doi: 10.1042/BJ20071166. PMID: 17941825. (Year: 2008).*
VectorBuilder. PBAD Recombinant Protein Vector. [online]. Sep. 19, 2020. [retrieved Jul. 3, 2023]. Retrieved from Internet <URL: https://en.vectorbuilder.com/resources/vector-system/pBAD.html> (Year: 2020).*
Du YL, and Ryan, KS. Pyridoxal phosphate-dependent reactions in the biosynthesis of natural products. Nat. Prod. Rep. 2019. 36, 430-457. DOI https://doi.org/10.1039/C8NP00049B (Year: 2019).*
Yang, J., Tan, G., Ting, Z., White, RH., Lu, J., & Ding, H. Deletion of the Proposed Iron Chaperones IscA/SufA Results in Accumulation of A Red Intermediate Cysteine Desulfurase IscS in *Escherichia coli*. J Biol Chem. 2015; 290(22), 14226-14234 (Year: 2015).*
Li et al CN110967305A_Claims_EN translation (Year: 2020).*

(Continued)

*Primary Examiner* — Michael Barker
*Assistant Examiner* — Georgiana C Reglas
(74) *Attorney, Agent, or Firm* — CHIESA, SHAHINIAN & GIANTOMASI PC

(57) ABSTRACT

The present disclosure provides a method for detecting L-serine based on cysteine desulfurase-containing living *Escherichia coli* cells, and belongs to the technical field of amino acid detection. The method includes the following steps: incubating an unknown sample with the cysteine desulfurase-containing living *E. coli* cells to produce a red substance, and qualitatively or semi-quantitatively detecting L-serine content in the unknown sample according to color changes of the red substance of the living *E. coli* cells, or quantitatively detecting L-serine content in the unknown sample by measuring absorbance of a lysate of the living *E. coli* cells. The detection method provided by the present disclosure is simple and convenient in process, few in reaction steps and stable in enzymatic activity of living cells.

6 Claims, 1 Drawing Sheet
Specification includes a Sequence Listing.

(56) References Cited

OTHER PUBLICATIONS

Li et al CN110967305A_Description_EN translation (Year: 2020).*
Kim et al Supplementary Information Sheet (Year: 2012).*
VectorBuilder WayBack Machine (Year: 2020).*
BioVision WayBack Machine (Year: 2017).*
Thornber C.W. Isosterism and Molecular Modification in Drug Design (Chem. Soc. Rev (1979) 8, p. 563-580) (Year: 1979).*

* cited by examiner

SEQUENCE LISTING

```
Sequence total quantity: 1
SEQ ID NO: 1          moltype = DNA  length = 1227
FEATURE               Location/Qualifiers
source                1..1227
                      mol_type = other DNA
                      note = Gene sequence encoding IscS
                      organism = synthetic construct
SEQUENCE: 1
atggaattac cgatttatct cgactactcc gcaaccacgc cggtggaccc gcgtgttgcc   60
gagaaaatga tgcagtttat gacgatggac ggaaccttg gtaacccggc ctcccgttct   120
caccgtttcg gctggcaggc tgaagaagcg gtagatatcg cccgtaatca gattgccgat   180
ctggtcggcg ctgatccgcg tgaaatcgtc tttacctctg gtgcaaccga atctgacaac   240
ctggcgatca aaggtgcagc caactttat cagaaaaaag gcaagcacat catcaccagc   300
aaaaccgaac acaaagcggt actggatacc tgccgtcagc tggagcgcga aggttttgaa   360
gtcacctacc tggcaccgca gcgtaacggc attatcgacc tgaaagaact tgaagcagcg   420
atgcgtgacg acaccatcct cgtgtccatc atgcacgtaa ataacgaaat cggcgtggtg   480
caggatatcg cggctatcgg cgaaatgtgc cgtgctcgtg gcattatcta tcacgttgat   540
gcaacccaga gcgtgggtaa actgcctatc gacctgagcc agttgaaagt tgacctgatg   600
tctttctccg gtcacaaaat ctatggcccg aaaggtatcg gtgcgctgta tgtacgtcgt   660
aaatcgcgcg tacgcatcga agcgcaaatg cacggcgggc gtcacgagcg cggtatgcgt   720
tccggcactc tgcctgttca ccagatcgtc ggaatgggcg aggcctatcg catcgcaaaa   780
gaagagatgg cgaccgagat ggaacgtctg cgcggcctgc gtaaccgtct gtggaacggc   840
atcaaagata tcgaagaagt ttacctgaac ggtgacctgg aacacggtgc gccgaacatt   900
ctcaacgtca gcttcaacta cgttgaaggt gagtcgctga ttatggcgct gaaagacctc   960
gcagtttctt caggttccgc ctgtacgtca gcaagcctcg aaccgtccta cgtgctgcgc  1020
gcgctggggc tgaacgacga gctggcacat agctctatcc gtttctcttt aggtcgtttt  1080
actactgaag aagagatcga ctacaccatc gagttagttc gtaaatccat cggtcgtctg  1140
cgtgaccttt ctccgctgtg ggaaatgtac aagcagggcg tggatctgaa cagcatcgaa  1200
tgggctcatc atcatcatca tcattga                                     1227
```

METHOD FOR DETECTING L-SERINE BASED ON CYSTEINE DESULFURASE-CONTAINING LIVING ESCHERICHIA COLI CELL

CROSS REFERENCE TO RELATED APPLICATION

This patent application claims the benefit and priority of Chinese Patent Application No. 202111282167.8, filed on Nov. 1, 2021, the disclosure of which is incorporated by reference herein in its entirety as part of the present application.

TECHNICAL FIELD

The present disclosure relates to the technical field of amino acid detection, in particular to a method for detecting L-serine based on cysteine desulfurase-containing living *Escherichia coli* cells.

BACKGROUND ART

L-serine is a kind of polar amino acid, which belongs to the group of non-essential polar amino acids in the human body. It participates in the biosynthesis of human proteins, purines, pyrimidines and phospholipids, and plays an important role in immune regulation, tumor metabolism and other processes. It has been indicated that the content of L-serine in urine is expected to become a tumor marker for some cancers, which can be used to assist in diagnosing tumors or judging prognosis. In addition, L-serine is also widely used in amino acid infusions, nutritional additives and deluxe cosmetics. Therefore, providing a quick and easy detection method for determining the content of L-serine in mixed amino acids, especially a detection technology capable of eliminating the interference of D-serine, cycloserine, serine analogs and serine derivatives, is extremely important for the development and utilization of L-serine.

At present, methods for determining amino acid content inside and outside of China are mainly divided into instrumental methods, chromogenic methods, chemiluminescence methods, and enzymatic methods. Instrumental methods usually include high performance liquid chromatography (HPLC), gas chromatography-mass spectrometry (GC-MS), liquid chromatography-mass spectrometry (LC-MS), nuclear magnetic resonance (NMR), and automatic amino acid analyzer. The chromogenic methods include chromotropic acid-spectrophotometry, paper chromatography-spectrophotometry, and ninhydrin method. Chemiluminescence method is mainly capillary electrophoresis coupling with electrochemiluminescence. Enzymatic methods include serine aminotransferase method and cystathionine lyase method.

Among them, instrumental methods such as liquid chromatography, gas chromatography, and chromatography-mass spectrometry have good sensitivity and high accuracy, but require expensive equipment, specialized laboratories, professionally trained laboratory technicians, high maintenance costs, and relatively high laboratory consumables. As the most basic and traditional detection method, ninhydrin method is easy to operate and quick to react, but it has high requirements on reaction conditions, and requires precise control of reaction temperature, pH, and time. Moreover, the method has different sensitivities to different types of amino acids and is not suitable for analysis of samples that require high precision. Fluorescence quenching method can avoid the interference of most amino acids, but the sample needs to undergo complex phosphorylation pretreatment, and the detection result has a large error. The paper chromatography-spectrophotometry is easy to operate, but it is not suitable for the analysis and detection of large quantities of samples due to its poor stability. Chromotropic acid-spectrophotometry has fast reaction speed, simple operation, and high accuracy, but poor anti-interference ability.

Enzymatic methods have excellent specificity and accuracy, but the currently used enzymatic methods have many reaction steps and many factors that affect the determination, and the detection signal often cannot be directly observed or directly measured. In addition, enzymes have poor stability and are not easy to store. Therefore, it is very necessary to develop a living cell enzymatic method for determining L-serine which is simple and can be directly observed with the naked eye after the reaction.

INCORPORATION BY REFERENCE

Submitted with the present application is an electronically filed sequence listing via the Patent Center as an CML formatted sequence listing, entitled "GWP20220400808.xml", created Sep. 29, 2022, and 3,182 bytes in size. The sequence listing is part of the specification filed herewith and is incorporated by reference in its entirety.

SUMMARY

An objective of the present disclosure is to provide a method for detecting L-serine based on cysteine desulfurase-containing living *E. coli* cells. By incubating the cysteine desulfurase-containing living *E. coli* cells with L-serine, a new living cell detection method of L-serine is developed to realize qualitative or semi-quantitative detection with naked eyes, as well as quantitative detection of L-serine content.

To achieve the above objective, the present disclosure provides the following solution, the present disclosure provides a method for detecting L-serine based on cysteine desulfurase-containing living *E. coli* cells, including steps of: incubating an unknown sample with the cysteine desulfurase-containing living *E. coli* cells to produce a red substance, and qualitatively or semi-quantitatively detecting L-serine content in the unknown sample according to color changes of the red substance of the living *E. coli* cells, or quantitatively detecting L-serine content in the unknown sample by measuring absorbance of a lysate of the living *E. coli* cells.

Preferably, the unknown sample and the cysteine desulfurase-containing living *E. coli* cells may be mixed and incubated in a volume ratio of 1:(5-10).

Preferably, incubation conditions may be as follows: cells may be cultured at 32-37° C. and 200-250 rpm under shaking for 2-12 h.

Preferably, incubation of the unknown sample with the cysteine desulfurase-containing living *E. coli* cells to produce the red substance may be followed by directly observing whether a red color is generated with the naked eye and qualitatively determining whether the unknown sample contains L-serine, and comparing the depth of a generated red color with a colorimetric card constructed with an L-serine standard solution to semi-quantitatively determine a range of the L-serine content in the unknown sample.

Preferably, after the unknown sample is incubated with the cysteine desulfurase-containing living *E. coli* cells to produce the red substance, a supernatant is collected by sonication and centrifugation, absorbance of the supernatant is measured, and the absorbance is substituted into a standard curve constructed by the L-serine standard solution to quantitatively determine the L-serine content in the unknown sample.

Preferably, the cysteine desulfurase-containing living *E. coli* cells may be prepared by the following steps:

transforming a pBAD expression vector pBISCS containing cysteine desulfurase IscS into *E. coli* MC4100 to construct a pBISCS/MC4100 strain;

inoculating the pBISCS/MC4100 strain into LB broth supplemented with ampicillin to obtain a bacterial suspension with an $OD_{600}$ of 0.6-0.8, and inducing the bacterial suspension with L-arabinose for 2-3 h to harvest cells; and washing the cells once or twice with M9 Buffer, and resuspending the cells in M9 Buffer supplemented with chloramphenicol and ampicillin to obtain the cysteine desulfurase-containing living *E. coli* cells.

Preferably, a gene sequence encoding the cysteine desulfurase IscS is shown in SEQ ID NO: 1.

The present disclosure provides the following technical effects:

According to the inventors' previous research, it is found that *E. coli* cysteine desulfurase is expressed in an IscA/SufA double-deficient bacterium. The enzyme turns red when observed with the naked eye, and there is a stable characteristic absorption peak at 528 nm when scanned by the UV-Vis spectrophotometer, but the mechanism of intracellular production of the red substance is not clear. Through further in-depth research, it is found that a main factor for the production of this stable red substance in cells is L-serine, and more importantly, the depth of redness and the height of the absorption peak at 528 nm show a dose-dependent relationship with the L-serine added in the medium. Based on this original discovery, the inventors optimize an L-serine enzymatic detection technology, and develop a method for detecting L-serine based on cysteine desulfurase-containing living *E. coli* cells in the present application.

Specifically, in the present disclosure, an L-serine sample is incubated with the cysteine desulfurase-containing living *E. coli* cells to produce a red substance, and the L-serine in the sample is qualitatively and quantitatively determined by the color depth of the red substance or by measuring the absorbance of a bacterial cell lysate at 528 nm. The process designed by the present disclosure is simple, with few reaction steps and stable enzyme activity in living cells. Not only can the process achieve intuitive qualitative detection and precise quantification, but also can effectively prevent the interference of D-serine, cycloserine, serine analogs and other amino acids.

BRIEF DESCRIPTION OF THE DRAWINGS

In order to illustrate the examples of the present disclosure or the technical solution in the prior art more clearly, the accompanying drawings required in the examples will be briefly introduced below. Obviously, the drawings in the following description are only some of the present disclosure. Other drawings can also be obtained by those of ordinary skill in the art without creative work based on these drawings.

DETAILED DESCRIPTION OF THE EMBODIMENTS

Figure 1:
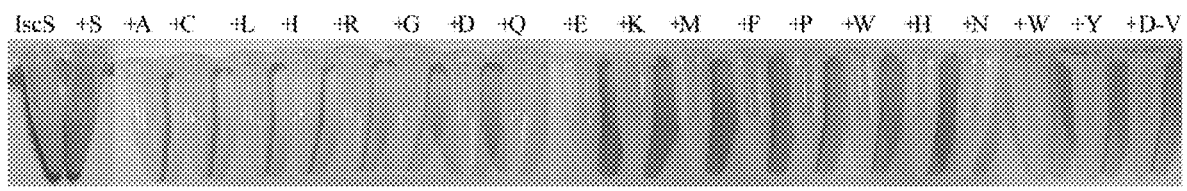
FIG. 1 illustrates the results of reactions of different amino acids with whole cells, where IscS is a control without amino acid addition, the capital letters after "+" are the abbreviations of amino acid types, and configurations thereof are all L-configurations.

The technical solution of the present disclosure will now be specifically described by way of examples. However, they should not be construed as limiting the present disclosure, but should be understood as more detailed descriptions of certain aspects, characteristics and embodiments of the present disclosure.

The test methods used in the following examples are conventional methods unless otherwise specified; the materials and reagents used are commercially available reagents and materials unless otherwise specified.

Example 1 Method for Quantitatively Detecting L-Serine Based on Cysteine Desulfurase-Containing Living *E. coli* Cells 1. Reactive Live Cell Preparation:

A pBAD expression vector pBISCS containing cysteine desulfurase IscS (the gene sequence encoding IscS is shown in SEQ ID NO: 1) was transformed into *E. coli* MC4100, namely a pBISCS/MC4100 strain, designated WMU-013.

The preserved *E. coli* WMU-013 was inoculated into LB broth containing 100 μg/mL ampicillin, and cultured at 37° C. and 250 rpm for 12-16 h overnight under shaking, and the bacterial suspension cultured overnight was diluted 1:100 to 500 mL of freshly prepared LB broth containing 100 μg/mL ampicillin; under the same conditions, the system was continued to culture until $OD_{600}$ nm was 0.6; after being induced with 0.02% L-arabinose for 3 h, the cells were collected by centrifugation, washed with 50 mL of M9 Buffer (12.8 g/L $Na_2HPO_4 \cdot 7H_2O$, 3 g/L $KH_2PO_4$, 0.5 g/L NaCl, and 1 g/L $NH_4Cl$) once, resuspended in the same buffer (250 mL) supplemented with 34 mg/mL chloramphenicol and 100 mg/mL ampicillin, and aliquoted in 50 mL/part for later use.

SEQ ID NO: 1:
ATGGAATTACCGATTTATCTCGACTACTCCGCAAC

CACGCCGGTGGACCCGCGTGTTGCCGAGAAAATGA

TGCAGTTTATGACGATGGACGGAACCTTTGGTAAC

CCGGCCTCCCGTTCTCACCGTTTCGGCTGGCAGGC

TGAAGAAGCGGTAGATATCGCCCGTAATCAGATTG

CCGATCTGGTCGGCGCTGATCCGCGTGAAATCGTC

TTTACCTCTGGTGCAACCGAATCTGACAACCTGGC

GATCAAAGGTGCAGCCAACTTTTATCAGAAAAAAG

GCAAGCACATCATCACCAGCAAAACCGAACACAAA

GCGGTACTGGATACCTGCCGTCAGCTGGAGCGCGA

-continued

```
AGGTTTTGAAGTCACCTACCTGGCACCGCAGCGTA

ACGGCATTATCGACCTGAAAGAACTTGAAGCAGCG

ATGCGTGACGACACCATCCTCGTGTCCATCATGCA

CGTAAATAACGAAATCGGCGTGGTGCAGGATATCG

CGGCTATCGGCGAAATGTGCCGTGCTCGTGGCATT

ATCTATCACGTTGATGCAACCCAGAGCGTGGGTAA

ACTGCCTATCGACCTGAGCCAGTTGAAAGTTGACC

TGATGTCTTTCTCCGGTCACAAAATCTATGGCCCG

AAAGGTATCGGTGCGCTGTATGTACGTCGTAAATC

GCGCGTACGCATCGAAGCGCAAATGCACGGCGGCG

GTCACGAGCGCGGTATGCGTTCCGGCACTCTGCCT

GTTCACCAGATCGTCGGAATGGGCGAGGCCTATCG

CATCGCAAAAGAAGAGATGGCGACCGAGATGGAAC

GTCTGCGCGGCCTGCGTAACCGTCTGTGGAACGGC

ATCAAAGATATCGAAGAAGTTTACCTGAACGGTGA

CCTGGAACACGGTGCGCCGAACATTCTCAACGTCA

GCTTCAACTACGTTGAAGGTGAGTCGCTGATTATG

GCGCTGAAAGACCTCGCAGTTTCTTCAGGTTCCGC

CTGTACGTCAGCAAGCCTCGAACCGTCCTACGTGC

TGCGCGCGCTGGGGCTGAACGACGAGCTGGCACAT

AGCTCTATCCGTTTCTCTTTAGGTCGTTTTACTAC

TGAAGAAGAGATCGACTACACCATCGAGTTAGTTC

GTAAATCCATCGGTCGTCTGCGTGACCTTTCTCCG

CTGTGGGAAATGTACAAGCAGGGCGTGGATCTGAA

CAGCATCGAATGGGCTCATCATCATCATCATCATT

GA
```

2. Preparation of 1 M L-Serine Standard

3. Determination of Optimal Incubation Time and Linear Range

A. Determination of Incubation Time

Unknown L-serine (4 mM) was mixed with the living cell suspension in a ratio of 1:10, and cultured at 37° C. and 250 rpm for different times under shaking; the cells were sonicated and centrifuged to take the supernatant, and the absorbance of the supernatant at 528 nm was measured, and a curve was plotted with time as the horizontal axis and the absorbance value at 528 nm as the vertical axis.

B. Determination of Linear Range

The L-serine standard solutions of a series of concentrations were mixed with the living cell suspension, and incubated at 37° C. and 250 rpm for 3 h under shaking; the color depth was observed with the naked eye and photographed to establish a colorimetric card; the cells were sonicated and centrifuged to take the supernatant, and the absorbance of the supernatant at 528 nm was measured, and a concentration-dependent curve was plotted with concentration as the horizontal axis and the absorbance value at 528 nm as the vertical axis.

4. Plotting of a Standard Curve

A standard curve was plotted with the concentration of the standard solution as the abscissa and the absorbance at 528 nm as the ordinate, and curve fitting was conducted to obtain a curve equation and an $R^2$ value.

5. Quantification of the Concentration of the Unknown Sample

The L-serine concentration in the unknown sample was obtained according to the equation and the absorbance value of the unknown sample tube.

6. Results and Analysis

The naked eye observation and the results of the colorimetric card showed that after the standard L-serine in the concentration range of 0-1 mM reacted with the living cell suspension, the color turned from pale yellow to pale pink and gradually darkened to red. By observing with the naked eye, the color change had good discrimination, and different colors and their depths could reflect the presence or absence of L-serine well, as well as the level of concentration. It can be seen that the experimental method for qualitative/semi-quantitative detection of L-serine of the present disclosure is feasible, convenient and efficient.

Figure 2A:
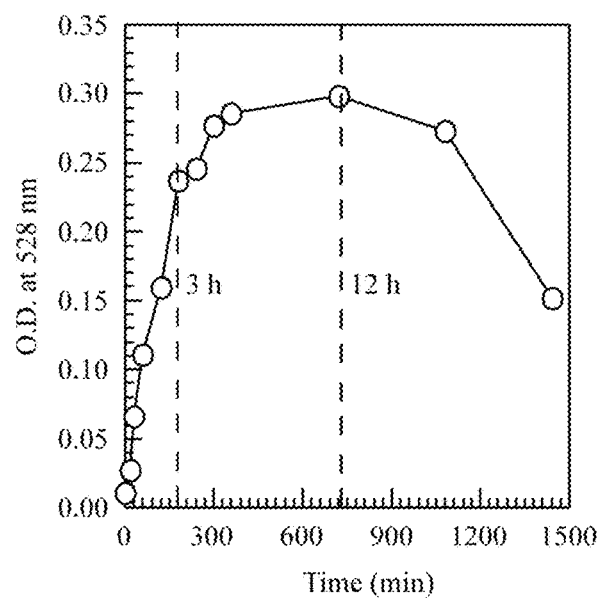
FIGS. 2A and 2B illustrate the determination of the optimal incubation time and linear range; panel A is the determination of the optimal incubation time, where excess L-serine (4 mM) is added to react for different times, then the obtained products are taken out for absorbance measurement at 528 nm to plot a curve over time; panel B is determination of the optimal linear range, where different concentrations of amino acids react with living cells for 3 h, and the absorbance is measured at 528 nm to plot a concentration-dependent curve.

As shown in FIG. 2A, L-serine responds quickly after incubation with the living cell suspension, shows a linear increase within 0-3 h, then plateaus stably, and decreases after 12 h. In order to reduce the measurement time, 3 h was selected as the optimal incubation time.

Figure 2B:
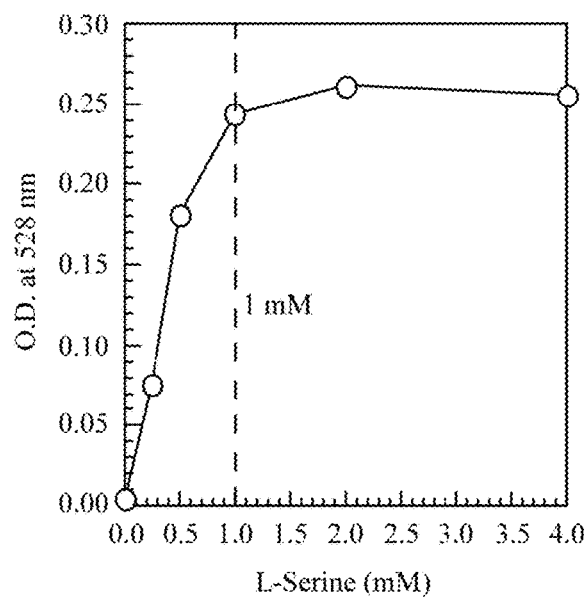

As shown in FIG. 2B, different concentrations of L-serine are incubated with living cell suspensions for 3 h, and the absorbance at 528 nm representing a red color in the supernatant gradually increases with the increase of L-serine concentration, and increases linearly in the concentration range of 0-1 mM, and then plateaus. Thus, it can be seen that the linear range of L-serine is 0-1 mM.

Example 2 Detection of the Ability to Resist the Interference of Other Amino Acids 500 μL each of unknown L-serine and other L-amino acids (4 mM) were mixed with 500 μL of living cell suspensions, respectively, and incubated on a shaker at 37° C. and 250 rpm for 3 h, and the color depth was observed with the naked eye and photographed.

Only L-serine appears red only after incubation with the living cell suspension (shown as dark gray +S vial of FIG. 1), and other amino acids and the control without amino acids all appear pale yellow, indicating that this method can directly observe the generation of red (shown as dark gray +S vial of FIG. 1) with the naked eye to determine whether there is L-serine or not. At the same time, it is not difficult to analyze that this method has a good ability to resist the interference of other amino acids and has good specificity. In addition, other types of amino acids were also detected by this method. Experimental methods demonstrated that the method had an excellent ability to resist the interference of D-serine, cycloserine and serine derivatives. The above results show that the method is feasible to qualitatively detect L-serine in a simple and easy manner, and has excellent specificity.

The above examples are only intended to describe the preferred implementations of the present disclosure, but not to limit the scope of the present disclosure. Various alterations and improvements made by those of ordinary skill in the art based on the technical solution of the present disclosure without departing from the design spirit of the present disclosure shall fall within the scope of the appended claims of the present disclosure.

```
Sequence Listing Information:
 DTD Version: V1_3
 File Name: GWP20220400808.xml
 Software Name: WIPO Sequence
 Software Version: 2.1.2
 Production Date: 2022 Sep. 29
General Information:
 Current application/Applicant file reference: GWP20220400808
 Earliest priority application/IP Office: CN
 Earliest priority application/Application number: 202111282167.8
 Earliest priority application/Filing date: 2021 Nov. 1
 Applicant name: Wenzhou Medical College
 Applicant name/Language: en
Invention title: METHOD FOR DETECTING L-SERINE BASED ON CYSTEINE
DESULFURASE-CONTAINING LIVING ESCHERICHIA COLI CELL (en)
 Sequence Total Quantity: 1
Sequences:
 Sequence Number (ID): 1
 Length: 1227
 Molecule Type: DNA
 Features Location/Qualifiers:
  -source, 1..1227
   > mol_type, other DNA
   > note, Gene sequence encoding IscS
   > organism, synthetic construct
Residues:
atggaattac cgatttatct cgactactcc gcaaccacgc cggtggaccc gcgtgttgcc     60
gagaaaatga tgcagtttat gacgatggac ggaacctttg gtaacccggc ctcccgttct    120
caccgtttcg gctggcaggc tgaagaagcg gtagatatcg cccgtaatca gattgccgat    180
ctggtcggcg ctgatccgcg tgaaatcgtc tttacctctg gtgcaaccga atctgacaac    240
ctggcgatca aggtgcagc caactttat cagaaaaaag gcaagcacat catcaccagc    300
aaaaccgaac acaaagcggt actggatacc tgccgtcagc tggagcgcga aggttttgaa    360
gtcacctacc tggcaccgca gcgtaacggc attatcgacc tgaaagaact tgaagcagcg    420
atgcgtgacg acaccatcct cgtgtccatc atgcacgtaa ataacgaaat cggcgtggtg    480
caggatatcg cggctatcgg cgaaatgtgc cgtgctcgtg cattatcta tcacgttgat    540 gcaacccaga gcgtgggtaa actgcctatc gacctgagcc agttgaaagt tgacctgatg    600
tctttctccg gtcacaaaat ctatggcccg aaaggtatcg gtgcgctgta tgtacgtcgt    660
aaatcgcgcg tacgcatcga agcgcaaatg acggcggcg gtcacgagcg cggtatgcgt    720
tccggcactc tgcctgttca ccagatcgtc ggaatgggcg aggcctatcg catcgcaaaa    780
gaagagatgg cgaccgagat ggaacgtctg cgcggcctgc gtaaccgtct gtggaacggc    840
atcaaagata tcgaagaagt ttacctgaac ggtgacctgg aacacggtgc gccgaacatt    900
ctcaacgtca gcttcaacta cgttgaaggt gagtcgctga ttatggcgct gaaagacctc    960
gcagtttctt caggttccgc ctgtacgtca gcaagcctcg aaccgtccta cgtgctcgc   1020 gcgctggggc tgaacgacga gctggcacat agctctatcc gtttctcttt aggtcgtttt   1080
actactgaag aagagatcga ctacaccatc gagttagttc gtaaatccat cggtcgtctg   1140
cgtgaccttt ctccgctgtg ggaaatgtac aagcagggcg tggatctgaa cagcatcgaa   1200
tgggctcatc atcatcatca tcattga                                      1227
END
```

What is claimed is:

1. A method for detecting L-serine based on cysteine desulfurase-containing Escherichia coli cells, comprising steps of: incubating an unknown sample with cysteine desulfurase-containing living Escherichia coli cells to produce a red substance, and qualitatively or semi-quantitatively detecting L-serine content in the unknown sample according to color changes of the red substance of the living Escherichia coli cells, and quantitatively detecting L-serine content in the unknown sample by measuring absorbance of a lysate of the living Escherichia coli cells, wherein the cysteine desulfurase-containing living Escherichia coli cells express cysteine desulfurase IscS, and a gene sequence encoding the cysteine desulfurase IscS is shown in SEQ ID NO: 1.

2. The method for detecting L-serine based on cysteine desulfurase-containing Escherichia coli cells according to claim 1, wherein the unknown sample and the cysteine desulfurase-containing living Escherichia coli cells are mixed and incubated in a volume ratio of 1:(5-10).

3. The method for detecting L-serine based on cysteine desulfurase-containing Escherichia coli cells according to claim 1, wherein incubation conditions are as follows: cells are cultured at 32-37° C. and 200-250 rpm under shaking for 212 h.

4. The method for detecting L-serine based on cysteine desulfurase-containing Escherichia coli cells according to claim 1, wherein incubation of the unknown sample with the cysteine desulfurase-containing living Escherichia coli cells to produce the red substance is followed by directly observing whether a red color is generated with the naked eye and qualitatively determining whether the unknown sample contains L-serine, and comparing the depth of a generated red color with a colorimetric card constructed with an L-serine standard solution to semi-quantitatively determine a range of the L-serine content in the unknown sample.

5. The method for detecting L-serine based on cysteine desulfurase-containing Escherichia coli cells according to claim 1, wherein after the unknown sample is incubated with the cysteine desulfurase-containing living Escherichia coli cells to produce the red substance, a supernatant is collected by sonication and centrifugation, absorbance of the supernatant is measured, and the absorbance is substituted into a standard curve constructed by an L-serine standard solution to quantitatively determine the L-serine content in the unknown sample.

6. The method for detecting L-serine based on cysteine desulfurase-containing Escherichia coli cells according to claim 1, wherein the cysteine desulfurase-containing living Escherichia coli cells are prepared by the following steps:
- transforming a pBAD expression vector pBISCS containing cysteine desulfurase IscS into Escherichia coli MC4100 to construct a pBISCS/MC4100 strain;
- inoculating the pBISCS/MC4100 strain into LB broth supplemented with ampicillin to obtain a bacterial suspension with an $OD_{600}$ of 0.6-0.8, and inducing the bacterial suspension with L-arabinose for 2-3 h to harvest cells; and
- washing the cells once or twice with M9 Buffer, and resuspending the cells in M9 Buffer supplemented with chloramphenicol and ampicillin to obtain the cysteine desulfurase-containing living Escherichia coli cells.

* * * * *